United States Patent [19]  [11] 4,052,417
Slinkard et al.  [45] Oct. 4, 1977

[54] VAPOR PHASE OXIDATION OF BUTANE PRODUCING MALEIC ANHYDRIDE AND ACETIC ACID

[75] Inventors: William Earl Slinkard; Anthony Basil Baylis, both of Corpus Christi, Tex.

[73] Assignee: Celanese Corporation, New York, N.Y.

[21] Appl. No.: 629,440

[22] Filed: Nov. 6, 1975

[51] Int. Cl.$^2$ ............................................. C07D 307/60
[52] U.S. Cl. ........................... 260/346.75; 260/533 R; 252/435; 252/437
[58] Field of Search ..................... 260/346.8 A, 533 R

[56] References Cited

U.S. PATENT DOCUMENTS

| 2,294,130 | 9/1942 | Porter | 260/346.8 A |
| 2,649,477 | 8/1953 | Jacobs et al. | 260/346.8 A |
| 3,907,833 | 9/1975 | Slinkard et al. | 260/346.8 A |

OTHER PUBLICATIONS

Ai et al., Bulletin of the Chemical Soc. of Japan, vol. 44, pp. 3081–3085 (1971).

*Primary Examiner*—Henry R. Jiles
*Assistant Examiner*—Bernard Dentz
*Attorney, Agent, or Firm*—John A. Shedden

[57] ABSTRACT

A vapor phase process is provided for high yield conversion of $C_4$-hydrocarbons to maleic acid (anhydride) and acetic acid in the presence of a catalyst comprising a reduced calcined coprecipitate of a molybdenum compound and a phosphorus compound, and optionally the catalyst includes one or more compounds of metal elements selected from titanium, vanadium, niobium and bismuth.

10 Claims, No Drawings

VAPOR PHASE OXIDATION OF BUTANE PRODUCING MALEIC ANHYDRIDE AND ACETIC ACID

BACKGROUND OF THE INVENTION

Processes for the oxidation of organic compounds such as hydrocarbons in the presence or absence of catalysts are well known. There is continuing applied research activity devoted to achieving economically feasible oxidation processes for commercial scale operation.

U.S. Pat. No. 3,282,994 describes a method for the oxidation of butane in liquid phase. U.S. Pat. No. 3,607,925 provides a process for the production of acetic acid by oxidation of butene-2 with nitric acid in the presence of a vanadium catalyst. U.S. Pat. No. 3,644,512 discloses a process for converting butane to acetic acid in liquid phase in the presence of a soluble cobalt compound.

Processes for the oxidation of hydrocarbons in the vapor phase by means of oxygen-containing gases have not proven entirely satisfactory primarily due to the excessive formation of undesirable carbon oxides, and to the difficulty in maintaining control of the highly exothermic oxidation reaction. U.S. Pat. No. 3,395,159 provides an improved process wherein the oxidation of hydrocarbons is performed in a reactor system having fused vanadium oxide catalyst coated on the inner surface of the reactor, which system has the advantage of better temperature control and isothermal operation.

In J. Am. Chem. Soc., 62, 2312 (1940) there are reported several processes for vapor phase oxidation of naphthalene to a mixture of partial oxidation products which include naphthoquinone, phthalic anhydride, maleic anhydride and benzoic acid. The naphthalene oxidation processes are suitable for the production of phthalic anhydride, but are impractical for high yield conversion to maleic anhydride.

In practice the commercial processes for the oxidation of hydrocarbons are difficult to manage, and inevitably the yield of desired product is low in comparison to the yield of carbon oxides and other oxidation by-products. The economics of maleic anhydride production by oxidation of butene or benzene is deficient in this respect.

Accordingly, it is an object of the present invention to provide a commercially feasible process for oxidation of hydrocarbons.

It is another object of this invention to provide a vapor phase process for converting $C_4$-hydrocarbons into maleic acid anhydride.

It is another object of this invention to provide a process for oxidizing butane or butene to maleic acid and acetic acid with high conversion efficiency and with a low yield of organic by-products.

It is a further object of the present invention to provide a novel catalyst composition for vapor phase conversion of $C_4$-hydrocarbons into maleic acid and acetic acid.

Other objects and advantages shall become apparent from the following description and examples.

DESCRIPTION OF THE INVENTION

One or more objects of the present invention are accomplished by the provision of a process for producing maleic acid (anhydride) and acetic acid which comprises contacting $C_4$-hydrocarbon and oxygen in vapor phase with a reduced molybdenum catalyst, wherein said molybdenum catalyst is prepared by (1) reducing a calcined mixture of molybdenum compound coprecipitated with phosphorus compound, or by (2) reducing a calcined mixture of molybdenum compound and phosphorus compound coprecipitated with one or more compounds of metal elements selected from the group consisting of titanium, vanadium, niobium and bismuth.

By the term "reduced molybdenum catalyst" is meant a metal oxide catalyst in which the molybdenum ions substantially are in a valence state of 4 (e.g., $MoO_2$) when introduced into the reaction system.

By the term "coprecipitated" is meant the precipitation from aqueous solution of soluble molybdenum compound and soluble compound(s) of the other active catalyst elements. The term also includes catalyst compositions which are precipitated from an aqueous medium in which one active catalyst element is slurried (e.g., $MoO_3$) and the other active catalyst element is dissolved (e.g., $TiCl_4$).

A convenient form of water soluble molybdenum compound is the commercially available ammonium heptamolybdate. In a preferred embodiment, the catalyst composition is prepared by coprecipitating from solution calculated proportions of soluble molybdenum compound and phosphorus compound, and optionally soluble compound(s) of titanium, vanadium, niobium and/or bismuth. A particularly effective soluble form of these active catalyst elements is the oxalate. Other useful derivative forms are halides, hydroxides, lactates, tartrates, citrates, acetylacetonates, and the like. In some cases of catalyst preparation, the addition of one active catalyst element solution to a second active catalyst element solution yields an immediate coprecipitation of catalyst elements. In other cases where coprecipitation is not spontaneous upon the blending of active catalyst element solutions, the coprecipitation is achieved by reducing the volume of aqueous medium.

The catalyst coprecipitate is recovered, dried and transformed into a powder having a particle size range between about 10 and 200 microns. The catalyst composition can also be prepared in the form of granules, pellets, and the like.

Another preferred method of preparing the invention catalyst is to coprecipitate the molybdenum and other active catalyst elements from solution onto a chemically inactive carrier such as α-alumina, silica, titanium oxide, Celite, diatomaceous earth, carborundum, silica-alumina, boria, or other convenient support.

When preparing a supported molybdenum catalyst composition, the molybdenum content, calculated as the free metal, ranges between about 0.1 and 10 weight percent, based on the total weight of the supported catalyst. Instead of impregnating a gel of aluminum oxide and/or silicon oxide with the active catalyst elements, a mixed gel can be prepared by coprecipitation of all the oxides from a solutin containing the corresponding soluble compounds.

In the invention reduced molybdenum catalyst compositions the atomic ratio of molybdenum to phosphorus is in the range between about 20:1 and 1:1, and preferably in the range between about 12:1 to 3:1. In the invention reduced molybdenum catalyst compositions which optionally contain one or more other catalyst metal elements selected from titanium, vanadium, niobium and bismuth, the atomic ratio of molybdenum to the sum of other catalyst metal elements is in the range between about 20:1 and 1:1, and preferably in the range between about 12:1 and 1:1.

After a molybdenum catalyst composition is recovered in the form of a coprecipitate as described hereinabove, it is subjected to a calcination procedure to convert all of the active catalyst elements into the form of the corresponding oxides. The catalyst calcination is conducted in an air or nitrogen stream at a temperature between about 400° C and 650° C for a period of time between about 4 and 200 hours. A preferred calcination temperature is in the range between about 450° C and 600° C.

As a final step in the preparation of the invention molybdenum catalysts, the oxide composition which is recovered from the calcination treatment is converted into a higher state of catalytic activity by subjecting the said calcined composition to a reducing environment for a period of time between about 4 and 48 hours at a temperature in the range between about 300° C and 600° C. This reducing treatment is conveniently accomplished by flowing a reducing gas such as ammonia, sulfur dioxide, hydrogen, carbon monoxide, hydrocarbons, and the like, in contact with the calcined molybdenum catalyst composition.

In the present invention process for catalytically reacting $C_4$-hydrocarbons with oxygen to produce maleic acid selectively in high yield, a hydrocarbon stream containing components selected from normal and isobutanes and butenes is mixed with oxygen gas and contacted in vapor phase with the reduced molybdenum catalyst composition provided as an embodiment of the present invention. The optimum temperature for the reaction varies between about 180° C and 350° C, and generally in the range between about 225° C and 300° C. The reduced molybdenum catalyst can be maintained in either a fixed bed or a fluid bed.

The contact time between the $C_4$-hydrocarbons and the reduced molybdenum catalyst varies between about 0.5 and 5 seconds. A shorter contact time is advantageous if the process is to involve recycling of product stream effluent.

It is advantageous in the practice of the invention process to maintain the quantity of oxygen gas in the feed stream at a level which is the least required to convert efficiently the $C_4$-hydrocarbon stream to maleic acid and acetic acid. The quantity of oxygen gas in the feed stream usually is maintained in the range between about 0.05 and 5.0 mole per mole of $C_4$-hydrocarbons, and preferably in the range between about 0.1 and 3.0 moles.

In a preferred embodiment of the invention process, water is included in the feed stream. The presence of water vapor in the oxidation reaction system increases the yield of maleic acid and lowers the yield of carbon oxides.

The recovery of the product stream and the separation of the maleic acid and acetic acid from acetaldehyde and other by-products can be accomplished by conventional procedures. U.S. Pat. No. 3,624,148 describes a method for the separation of maleic acid from acetic acid.

The following examples are further illustrative of the present invention. The reactants and other specific ingredients are presented as being typical, and various modifications can be devised in view of the foregoing disclosure within the scope of the invention.

EXAMPLE A

Vapor Phase Oxidation Procedures

Standard screening conditions were a feed gas composition ratio of butane/oxygen/steam of 9/1/5 to 11/1/6 with a total flow rate of about 150 ml/minute. A pressure of 5-10 psig was maintained in each reactor. The reactor consisted of a U-shaped stainless steel tube (inside diameter about 1 centimeter) with the catalyst containing section about 55 centimeters long. Catalyst charges consisted of 10cc of 20/30 mesh material, or for supported catalyst, 30cc of 20/30 mesh material. Material balances were calculated over periods of 5-16 hours and entailed chemical analysis (gas chromatography and titration of acid with base) of liquid products collected in an ice-cooled trap. Oxygen and carbon oxides in the vent were analyzed of a Fisher-Hamilton gas partitioner and samples of the vent gas were analyzed for acetaldehyde and butenes by gas chromatography.

EXAMPLE B

| Preparation Of Catalysts | |
|---|---|
| 1. $Mo_{10}PO_x$ on $SiO_2$ Catalyst | |
| $MoO_3$ | 144.0 g |
| $H_3PO_4$ | 8.2 g |
| | (9.6 g of 85% phosphoric acid) |

$MoO_3$ and $H_3PO_4$ were refluxed together in 1 liter of water overnight and the unreacted $MoO_3$ (32.7 grams) removed by filtration. The bright yellow filtrate was concentrated to about 200 ml in volume and then the remaining water was removed by drying in an oven at 80° C. 100 grams of the dried solid were dissolved in enough water to equal 95 ml of solution. This solution was used to impregnate 100cc of macroporous silica beads. The impregnated beads were dried overnight at 80° C, calcined at 500° C for 18 hours, then reduced with hydrogen at 400° C for 16 hours.

| 2. $Mo_{12}Bi_{12}PO_x$ Catalyst | |
|---|---|
| $(NH_4)_6Mo_7O_{24}\cdot 4H_2O$ | 61.8 g |
| $Bi(NO_3)_3\cdot 5H_2O$ | 169.8 g |
| $H_3PO_4$ | 3.1 g |
| | (3.6 g of 85% phosphoric acid) |

$Bi(NO_3)_3\cdot 5H_2O$ was dissolved in 20 ml of conc. $HNO_3$ + 180 ml of water. $(NH_4)_6Mo_7O_{24}\cdot 4H_2O$ and $H_3PO_4$ were dissolved in 200 ml of water. The two solutions were added simultaneously to 100 ml of water with stirring together with ammonium hydroxide to maintain the pH of the reaction mixture at approximately 7. A precipitate formed immediately. The precipitate was collected by filtration, washed with water, dried and calcined at 540° C overnight followed by hydrogen reduction at 400° C for about 16 hours.

3. $Mo_{10}PO_x$ Catalyst

A commercially available sample of phosphomolybdic acid, $P_2O_5\cdot 20MoO_3\cdot 51H_2O$, was calcined overnight at 540° C and then reduced with hydrogen at 400° C for about 16 hours.

| 4. $Mo_{10}V_2PO_x$ Catalyst | |
|---|---|
| $NaVO_3\cdot O\cdot 4H_2O$ | 48.8 g |
| $Na_2HPO_4\cdot 7H_2O$ | 26.8 g |
| $Na_2MoO_4\cdot 2H_2O$ | 242 g |

To the $NaVO_3\cdot O\cdot 4H_2O$ dissolved in 200 ml of hot water was added $Na_2HPO_4\cdot 7H_2O$ dissolved in 200 ml of water. To this solution was added 10 ml of conc. $H_2SO_4$, followed by the $Na_2MoO_4 \cdot 2H_2O$ dissolved in 400 ml of water, and then 170 ml of conc. $H_2SO_4$. The now deep red solution was stirred for an additional two hours, cooled, and contacted with diethyl ether in a large separatory funnel to form three layers. The deep red middle layer was drawn off, the ether removed by heat as 100 ml of water was added, and then the water was removed on a rotary evaporator. The resulting solid was calcined at 540° C overnight and then reduced with hydrogen at 400° C for about 16 hours.

| 5. $Mo_{10}Nb_2PO_x$ Catalyst | |
|---|---|
| $Na_2MoO_4 \cdot 2H_2O$ | 121 g |
| $K_8Nb_6O_{19} \cdot 16H_2O$ | 23.8 g |
| $Na_2HPO_4 \cdot 7H_2O$ | 13.4 g |

To the $Na_2MoO_4 \cdot 2H_2O$ dissolved in 250 ml of water was added 125 ml of 6M HCl. To this solution was added in order: $K_8Nb_6O_{19} \cdot 16H_2O$ dissolved in 250 ml of water, $Na_2HPO_4$ dissolved in 100 ml of water, and then the pH of the reaction mixture was adjusted to about 5 with 50% HCl (1 part conc. HCl to 1 part $H_2O$ by volume). The reaction mixture was refluxed for 2 hours during which time all of the reagents dissolved. The solution was cooled, combined with an equal volume of 1M HCl, and contacted with n-butanol in a large separatory funnel. The organic layer was drawn off and butanol removed on a rotary evaporator. The resulting deep blue solid was calcined overnight at 500° C and then reduced with hydrogen at 400° C for about 16 hours.

| 6. $Mo_{10}P_2BiO_x$ Catalyst | |
|---|---|
| $(NH_4)_6Mo_7O_{24} \cdot 4H_2O$ | 247.2 g |
| $Bi(NO_3)_3 \cdot 5H_2O$ | 67.9 g |
| $H_3PO_4$ | 27.4 g (32.3 g of phosphoric acid) |

To the $(NH_4)_6Mo_7O_{24} \cdot 4H_2O$ and $H_3PO_4$ dissolved in 400 ml of water was added dropwise with stirring $Bi(NO_3)_3 \cdot 5H_2O$ dissolved in 100 ml of 50% $HNO_3$ (1 part conc. $HNO_3$ to 1 part $H_2O$ by volume). A precipitate formed immediately. After addition was complete, the water was removed on a rotary evaporator and the residue calcined at 500° C overnight followed by hydrogen reduction at 400° C for about 16 hours.

| 7. $Mo_{24}Ti_3P_2O_x$ Catalyst | |
|---|---|
| $Na_2MoO_4 \cdot 2H_2O$ | 295.0 g |
| $TiCl_4$ | 25.9 g |
| $C_5H_5N$ | 39.0 g |
| $Na_3PO_4 \cdot 12H_2O$ | 57.0 g |

$Na_3PO_4 \cdot 12H_2O$ dissolved in enough water to equal 500 ml of solution was added to $Na_2MoO_4 \cdot 2H_2O$ dissolved in 1 liter of water and the pH adjusted to 1 with conc. HCl. To this solution was added dropwise with stirring $TiCl_4$ dissolved in enough conc. HCl to equal 35 ml of solution. The combined solutions were diluted to 2000 ml with water and heated to 50° C for several minutes. To this solution was added dropwise with stirring pyridine dissolved in enough water to equal 400 ml of solution with the pH adjusted to 1 with conc. HCl. The resulting yellow crystalline precipitate was collected on filter, washed with cold water, and dried at 80° C. The dried solid was calcined overnight at 500° C and reduced with hydrogen at 400° C for about 16 hours.

| 8. $MoO_2/SiO_2$ Catalyst | |
|---|---|
| $(NH_4)_6Mo_7O_{24} \cdot 4H_2O$ | 225.5 g |
| $SiO_2$ | 22.0 g |

$(NH_4)_6Mo_7O_{24} \cdot 4H_2O$ was dissolved in 400 ml of hot water and added to the fumed silica to form a thin paste. The paste was dried at 90° C and then calcined under a hydrogen atmosphere at 400° C for about 18 hours.

EXAMPLE C

| Production of Maleic Acid And Acetic Acid | | | |
|---|---|---|---|
| Catalyst Preparation Reference | 1. | 2. | 3. |
| Catalyst Composition | $Mo_9PO_x$ on $SiO_2$ | $Mo_{12}Bi_{12}PO_x$ | $Mo_{10}PO_x$ |
| Reactor Temperature, ° C. | 264 | 295 | 295 |
| Oxygen Conversion, %[1] | 55–60 | 39 | 96 |
| Butane Conversion, %[2] | 1.5–1.7 | 1.0 | 1.9–2.4 |
| Carbon Efficiency, %[3] | | | |
| Butenes | 3.5–3.7 | 11 | 3.7–3.8 |
| Acetic acid | 33 | 20 | 25–28 |
| Acetaldehyde | 1.0–2.3 | 1.1 | 0.5–0.6 |
| Maleic acid | 19–21 | 35 | 26–27 |
| Acrylic acid | 1.1–1.4 | 4.3 | 5.2–5.7 |
| Formic acid | 1.3–1.5 | 1.1 | 0.4–0.9 |
| Carbon monoxide | 14–15 | 9.1 | 13–14 |
| Carbon dioxide | 23–24 | 16 | 22–23 |
| | | | |
| Catalyst Preparation Reference | 4. | 5. | 6. |
| Catalyst Composition | $Mo_{10}V_2PO_x$ | $Mo_{10}Nb_2PO_x$ | $Mo_{10}P_2BiO_x$ |
| Reactor Temperature, ° C. | 296 | 298 | 295 |
| Oxygen Conversion, %[1] | 21 | 33–34 | 16 |
| Butane Conversion, %[2] | 0.7 | 1.1–1.2 | 0.5 |
| Carbon Efficiency, %[3] | | | |
| Butenes | 8.2 | 22–27 | 17 |
| Acetic acid | 40 | 24–25 | 22 |
| Acetaldehyde | 4.7 | 1.7–2.7 | 3.9 |
| Maleic acid | 13 | 13 | 24 |
| Acrylic acid | 2.5 | 1.0–1.7 | 1.7 |
| Formic acid | 2.5 | 0.3 | 1.8 |
| Carbon monoxide | 18 | 8–13 | 16 |
| Carbon dioxide | 9.0 | 22–23 | 11 |
| | | | |
| Catalyst Preparation Reference | 7. | 8. | |
| Catalyst Compositon | $Mo_{24}Ti_3P_2O_x$ | $MoO_2/SiO_2$ | |
| Reactor Temperature, ° C. | 299 | 290 | |
| Oxygen Conversion, %[1] | 25 | no reaction | |
| Butane Conversion, %[2] | 1.0 | | |

EXAMPLE C-continued

Production of Maleic Acid And Acetic Acid

| Carbon Efficiency, %[3] | |
|---|---|
| Butenes | 33 |
| Acetic acid | 22 |
| Acetaldehyde | 4.7 |
| Maleic acid | 14 |
| Acrylic acid | 1.3 |
| Formic acid | 0.6 |
| Carbon monoxide | 12 |
| Carbon dioxide | 10 |

[1] Oxygen conversion = $\dfrac{\text{Moles oxygen in} - \text{moles oxygen out}}{\text{Moles oxygen in}} \times 100\%$

[2] Butane conversion = $\dfrac{\text{Moles butane in} - \text{moles butane out}}{\text{Moles butane in}} \times 100\%$

[3] Carbon efficiency is calculated on a carbon accounted for basis, e.g., carbon efficiency to acetic acid =
$\dfrac{\text{Moles of carbon recovered as acetic acid}}{\text{Total moles of carbon recovered in products}} \times 100\%$

What is claimed is:

1. A process for producing maleic acid anhydride which comprises contacting butane, oxygen in the range between about 0.05 and 5.0 mol per mol of butane and water in the vapor phase at a temperature between about 180° C and 350° C with a reduced molybdenum catalyst wherein said molybdenum catalyst consists essentially of a catalyst prepared by reducing a calcined mixture of molybdenum compound coprecipitated with phosphorus compound.

2. A process in accordance with claim 1 wherein the atomic ratio of molybdenum to phosphorus is in the range between about 20:1 and 1:1.

3. A process in accordance with claim 1 wherein the catalyst is supported on a carrier.

4. A process in accordance with claim 1 wherein the contact time of butane with the catalyst is between about 0.5 and 5 seconds.

5. A process in accordance with claim 1 wherein the resulting product mixture substantially comprises maleic acid anhydride and acetic acid.

6. A process for producing maleic acid anhydride which comprises contacting butane, oxygen in the range between about 0.05 and 5.0 mol per mol of butane and water in the vapor phase at a temperature between about 180° C and 350° C with a reduced molybdenum catalyst wherein said molybdenum catalyst consists essentially of a catalyst prepared by reducing a calcined mixture of a molybdenum compound and phosphorus compound coprecipitated with one or more metal compounds selected from the group consisting of a bismuth compound and a niobium compound.

7. A process in accordance with claim 6 wherein the atomic ratio of molybdenum to the sum of other metal elements selected from the group consisting of niobium and bismuth is in the range between 20:1 and 1:1.

8. A process in accordance with claim 6 wherein the catalyst is supported on a carrier.

9. A process in accordance with claim 6 wherein the contact time of butane with the catalyst is between about 0.5 and 5 seconds.

10. A process in accordance with claim 6 wherein the resulting product mixture substantially comprises maleic acid anhydride and acetic acid.

* * * * *